United States Patent
Huang et al.

(10) Patent No.: US 10,321,677 B2
(45) Date of Patent: *Jun. 18, 2019

(54) COMPOSITIONS, ADDITIVES, AND METHODS FOR MITIGATING OR CONTROLLING SEED DUST

(71) Applicant: Bayer CropScience LP, Research Triangle Park, NC (US)

(72) Inventors: Yaodong Huang, Cary, NC (US); William Hanson, Wake Forest, NC (US); Philip M. Mathew, Morrisville, NC (US); Smita Patel, Raleigh, NC (US); Justin Eldridge, Durham, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/891,638

(22) Filed: Feb. 8, 2018

(65) Prior Publication Data

US 2018/0160678 A1 Jun. 14, 2018

Related U.S. Application Data

(63) Continuation of application No. 14/198,075, filed on Mar. 5, 2014, now abandoned.

(60) Provisional application No. 61/799,526, filed on Mar. 15, 2013.

(51) Int. Cl.
*A01N 25/00* (2006.01)
*A01N 3/00* (2006.01)
*A01N 51/00* (2006.01)
*A01N 43/40* (2006.01)
*A01N 47/40* (2006.01)

(52) U.S. Cl.
CPC ............ *A01N 3/00* (2013.01); *A01N 25/00* (2013.01)

(58) Field of Classification Search
None
See application file for complete search history.

(56) References Cited

U.S. PATENT DOCUMENTS

| | | | |
|---|---|---|---|
| 3,740,419 A | 6/1973 | Campbell | |
| 5,674,517 A * | 10/1997 | Carpenter | A01N 25/04 424/405 |
| 5,997,946 A | 12/1999 | Bell et al. | |
| 2009/0137607 A1 | 5/2009 | Holder et al. | |
| 2011/0033436 A1 | 2/2011 | Chen et al. | |
| 2012/0202689 A1 | 8/2012 | Dorr et al. | |
| 2013/0109725 A1 | 5/2013 | Dave et al. | |

FOREIGN PATENT DOCUMENTS

| | | |
|---|---|---|
| WO | 2007051249 A1 | 5/2007 |
| WO | 2011/045004 A2 | 4/2011 |
| WO | 2012076567 A2 | 6/2012 |
| WO | 2012125468 A2 | 9/2012 |
| WO | 2012168210 A1 | 12/2012 |
| WO | 2013166012 A1 | 11/2013 |

OTHER PUBLICATIONS

International Search Report dated Dec. 22, 2014, issued in counterpart Application No. PCT/US2014/033815.
BASF "PVP and more . . . " LUVITEC, LUVICROSS, and COLLACRAL VAL: Versatile Special Polymers for technical Application p. 1-20.

* cited by examiner

*Primary Examiner* — Katherine Peebles

(57) ABSTRACT

The disclosure provides for methods for reducing dust by treating a seed with a dust reducing composition described herein. The disclosure also provides for methods of reducing exposure to vacuum planter dust released during seed planting by applying a composition described herein to a seed. Methods for increasing seed lubricity by coating a seed with a composition described herein are also provided for. Compositions and seeds useful in these methods are also described.

12 Claims, No Drawings

COMPOSITIONS, ADDITIVES, AND METHODS FOR MITIGATING OR CONTROLLING SEED DUST

CROSS REFERENCE TO RELATED APPLICATION

This is a continuation application of U.S. patent application Ser. No. 14/198,075, filed Mar. 5, 2014, which claims the benefit of U.S. Provisional Application Ser. No. 61/799,526, filed Mar. 15, 2013, the content of which is incorporated by reference in its entirety.

FIELD

The disclosure provides for compounds, compositions, and methods of reducing dust, for example seed dust, by utilizing a dust reducing composition described herein. The disclosure also provides for methods of reducing seed dust associated with the treatment, coating, processing, transportation, storage, and/or planting of seeds by treating a seed with a composition described herein. Methods and compositions for improving the homogeneity and dispersion of an active agent on a seed surface are also provided. The disclosure also provides for methods of treating or washing a seed prior, during the same time as, or after treatment of a seed with a seed treating agent. Seeds and compositions useful in these methods are also described.

BACKGROUND

There is a need to develop new techniques for reducing and/or mitigating the amount of seed dust associated with the treatment, coating, and planting of seeds. Depending on the type of seed coating or treatment employed, seed dust can accumulate during a variety of situations associated with the processing, shipping, and/or planting of seeds. For instance, in situations where seeds are pre-treated with a coating agent or composition, placed into bags and shipped to a location, seed dust can accumulate in seed bags due to seed-to-seed and/or seed-to-bag interactions. Seed dust can also accumulate during the storage or handling of seed or seed bags. As such, there is a need to find an alternative to traditional seed coatings that are capable of limiting dust associated with the treating, coating, planting, and/or shipping of seeds. To this end, the disclosed compositions and methods have the ability to reduce and mitigate seed dust in a manner that was not previously recognized.

SUMMARY

In an aspect, the disclosure provides for a method of reducing or controlling seed dust by treating a seed with a dust reducing composition including:

(a) one or more active agent selected from the group consisting of an insecticide, pesticide, and, fungicide; and (b) at least one dust reducing agent selected from the group consisting of oil, a wetting agent, a dispersing agent, a film forming compound, a binder, and combinations thereof.

In another aspect, the disclosure provides for method of improving the homogeneity and dispersion of an active agent on a seed by treating a seed with a dust reducing composition including:

(a) one or more active agent selected from the group consisting of an insecticide, pesticide, and, fungicide; and (b) at least one dust reducing agent selected from the group consisting of oil, a wetting agent, a dispersing agent, a film forming compound, a binder, and combinations thereof.

In yet another aspect, the disclosure provides for a washing and/or cleaning a seed by treating a seed with a composition described herein including one or more dust reducing components selected from the group consisting of oil, a wetting agent, a dispersing agent, a film forming compound, a binder, and combinations thereof.

The disclosure also provides for methods of reducing seed dust associated with the treatment, coating, processing, transportation, storage, and/or planting of seeds by treating a seed with a composition described herein.

In yet another aspect, the disclosure provides for seed additive composition or a method of adding a dust reducing composition as an additive by treating a seed with a dust reducing composition including one or more dust reducing components selected from the group consisting of oil, a wetting agent, a dispersing agent, a film forming compound, a binder, and combinations thereof.

In another aspect, the disclosure provides for a dust reducing composition including:

(a) an active agent selected from the group consisting of an insecticide, pesticide, and fungicide; and (b) a dust reducing agent selected from the group consisting of oil, a wetting agent, a dispersing agent, a film forming compound, a binder, and combinations thereof.

In another aspect, the disclosure provides for a coated seed including:

(a) an active agent selected from the group consisting of an insecticide, pesticide, and fungicide; and (b) a dust reducing agent selected from the group consisting of oil, a wetting agent, a dispersing agent, a film forming compound, a binder, and combinations thereof.

In an aspect, the active agent is selected from the group consisting of acetamiprid, clothianidin, dinotefuran, imidacloprid, nitenpyram, thiacloprid, thiamethoxam, and combinations thereof.

In an aspect, a seed described herein is selected from the group consisting of a corn seed, cotton seed, sorghum seed, oat seed, rye seed, rice seed, rapeseed, canola seed, barley seed, soybean seed, and vegetable seed.

In another aspect, the seed is treated with the dust reducing composition prior to planting.

In yet another aspect, the seed is treated with the dust reducing composition at the same time as planting or after planting. In an aspect, the seed is planted with a mechanical planter.

In yet another aspect, the dust reducing composition includes one or more dust reducing agents selected from the group consisting of:

(a) poly(vinyl alcohol)/poly(vinyl pyrrolidone)copolymer;

(b) polyurethane composition or dispersion;

(c) ethoxylated fatty acid;

(d) sorbitan monooleate;

(e) alkyl alcohol with a ethylene oxide/propylene oxide;

(d) ethoxylated oleyl alcohol; and (g) oil.

In another aspect, a composition capable of being used in the methods described herein include one or more of the compounds or compositions set forth in the Tables, Figure, or Examples. In another aspect, a composition capable of being used in the methods described herein include one or more of the compounds or compositions set forth in Tables 1-4 and 6.

DETAILED DESCRIPTION

Methods of Reducing Seed Dust

The disclosure provides for compositions and methods for reducing, controlling, and/or mitigating seed dust. The disclosure also provides for compounds, compositions, and methods of reducing dust, for example seed dust, by utilizing a dust reducing composition described herein.

In an aspect, the disclosure provides for a method of reducing dust, for example, pesticidal dust, insecticidal dust, and/or fungicidal dust. In another aspect, the disclosure provides for a method of reducing dust emission, pesticidal dust, insecticidal dust, and/or fungicidal dust by treating or coating a seed with a composition described herein. In yet another aspect, the disclosure provides for a method of reducing dust emission, pesticidal dust, insecticidal dust, or fungicidal dust by:

(1) applying an active agent, such as a pesticide, insecticide, or fungicide to a seed; and
(2) applying a composition described herein to the treated seed such that the composition reduces dust emission, pesticidal dust, insecticidal dust, herbicidal and/or fungicidal dust.

In another aspect, the disclosure provides for a method of reducing seed dust associated with the treatment, coating, processing, transportation, storage, and/or planting of seeds by treating a seed with a composition described herein. In another aspect, the seed is treated with a compound or composition described herein prior, at the same time as, or after treatment of a seed with an active agent, for example, a pesticide, insecticide, or fungicide.

In yet another aspect, the disclosure provides for a method of storing a seed or increasing the storage stability of a seed, for example a seed pre-treated prior to planting, by treating a seed with a compound or composition described herein. In yet another aspect, the seed can be treated with a compound or composition described herein anytime the seed is handled by an individual or transported. The dust reducing compounds and compositions described herein reduce seed dust, thereby providing an improved method of handling and/or transporting seeds.

In another aspect, the disclosure provides for a method of treating a seed with a composition described herein by immobilizing or stabilizing at least one active ingredient on a seed surface, isolating or protecting at least one active ingredient on a seed surface, or delivering at least one active ingredient into a seed. In yet another aspect, the disclosure provides for a method of treating a seed via the methodology described herein.

In an aspect, the disclosure provides for a method of treating or coating a seed with a treating agent and a composition described herein wherein the coated seed emits a reduced amount of dust, pesticidal dust, insecticidal dust, or dust. In other aspects, compositions described herein The disclosure also provides for a method of reducing dust emission, pesticidal dust, insecticidal dust, herbicidal and/or fungicidal dust by utilizing a composition described herein to disperse active agents described herein on a seed surface.

The disclosure also provides for a method of reducing vacuum planter dust released during planting. In an aspect, the disclosure provides for a method of reducing insect exposure to vacuum planter dust released during planting. In another aspect, the vacuum planter dust is an insecticidal, pesticidal, or fungicidal dust.

In an aspect, the disclosure provides for a method of improving seed flow by applying or treating seed with a composition described herein. In another aspect, a composition described herein is applied to wet seed. The disclosure also provides for a method of increasing seed lubricity by coating a seed with a composition described herein. In an aspect, the disclosure provides for a method of lowering lubricity at lower use rates than those afforded by the coating of a seed with talc or graphite. The disclosure also provides for a method increasing the level of lubricity in an amount that is sufficient to reduce seed attrition that may result in the loss of small amounts of insecticide from the seed surface.

The disclosure also provides for a method of adding a treating agent together with a composition described herein to a seed. In another aspect, a composition described herein is added to a pre-treated seed prior to the pre-treated seed being placed in soil. In another aspect, a seed is pre-treated by both a treating agent and a composition described herein prior to planting. In yet another aspect, a composition described herein can be applied to seed in a planter or hopper either manually or with a mechanized system, such as a mechanized metering system. In an aspect, the powder form of a composition described herein is added to seed in a planter.

In an aspect, a composition herein is added to a seed prior to placing seed into a bag or container for shipping to a planting site. In another aspect, after the seed arrives at the planting site, a composition described herein is added to the seed. In yet another aspect, a composition described herein is added to pre-treated seed (seed previously treated with a treating agent) in a planter mechanism or hopper of the planting mechanism. In another aspect, a treating agent and a composition described herein are added to a seed prior to the seed being loaded on a planter or hopper for planting. In yet another aspect, a treating agent and a first composition described herein are added to seed prior to the seed being loaded on a planter or hopper for planting and a second, third, fourth, fifth, or sixth composition described herein is added to seed in the planter or hopper.

In an aspect, the dust, insecticidal dust, herbicidal dust, pesticidal dust, or fungicidal dust emission is reduced relative to traditional lubricants, such as talc or graphite. In yet another aspect, a lubricant composition described herein, for example a wax composition, reduces the dust, insecticidal dust, herbicidal dust, pesticidal dust, or fungicidal dust emission from the planter mechanism, such as an air or vacuum planter. In an aspect, the planter mechanism is a John Deere, Case IH, Kinze, AGCO White, Great Plains, or Precision Planting vacuum planter.

The disclosure also provides for a method of reducing active agent dust, pesticide, herbicidal, fungicide, or insecticide dust exposure to an insect by applying a composition described herein to a seed. In an aspect, the insect can be a pollinating insect. In another aspect, the insect is a bee. Bees are insects of the Order Hymenoptera, Superfamily Apoidea. In another aspect, the bee is a honey bee (*Apis*). In another aspect, the bee is a European honey bee (*Apis mellifera*) or Africanized honey bee. Examples of common bees are bumble bees (*Bomzbus*), small carpenter bees (*Ceratina*), large carpenter bees (*Xylocopa*), paper wasps (*Polistes*), yellow jackets (*Vespula*), and baldfaced hornets (*Vespula*). As used herein, the term "honey bee" can refer to any member of the Order Hymeoptera, Family Apidae, and includes, without limitation, *Apis andreniformis, Apis cerana, Apis dorsata, Apis florae, Apis mellifera, Apis koschevnikovi, Apis laboriosa, Apis nigrocincta, Apis rorea,* subspecies thereof, and strains, varieties, and hybrids thereof.

Method of Washing, Cleaning, or Utilizing a Seed as an Additive

Methods and compositions for improving the homogeneity and dispersion of an active agent on a seed surface comprising, consisting of, or consisting essentially of treating a seed with one or more compositions described herein.

The disclosure also provides for methods of treating or washing a seed comprising, consisting of, or consisting essentially of treating a seed with one or more compositions described herein. In another aspect, the seed is cleaned and/or washing with a composition described herein, such as a wetting agent, prior, during the same time, or after treatment of a seed with a seed treating agent. In an aspect, the method or washing or cleaning a seed treating a seed with a composition described herein can be supplemented or combined with any convention seed cleaning or washing methods, for example, applying air flow to a seed. In another aspect, a method of cleaning or washing a seed does not include cleaning or washing by air flow.

In an aspect, a seed is washed or cleaned prior to being placed in a slurry or treatment composition. In another aspect, the disclosure provides for a method of utilizing a compound or composition in a slurry.

In another aspect, a composition described herein is an additive in a seed treatment process. In yet another aspect, a composition described herein can be utilized as an additive in the seed coating process at any time during the coating, handling, and/or planting of a seed.

In an aspect, a composition capable of being used with the methods described herein comprises, consists essentially of, or consists of a composition described herein. In another aspect, a composition capable of being used with the methods described herein comprises, consists essentially of, or consists of a composition described herein and treating agent described herein.

Dust Reducing and Additive Compositions

The dust reducing compounds and compositions described herein can be used together with any of the methods described herein. For example, without being limited, the dust reducing compositions described herein can be used in a method of reducing seed dust associated with the treatment, coating, processing, transportation, storage, and/or planting of seeds. The disclosure also provides for a method of utilizing the dust reducing compositions as an additive or during a seed washing or cleaning process. The disclosure also provides for utilizing the dust reducing compositions described herein in a slurry, for example, a seed treatment slurry, with or without the addition of an insecticide, pesticide, or fungicide compound or composition.

In an aspect, the disclosure provides for compositions capable of dispersing an active agent on a seed surface and methods thereof. In yet another aspect, compositions described herein are capable of achieving improved active agent uniformity on a seed surface thereby yielding treated seeds with a reduced dust content. In another aspect, the dust reducing compositions provided herein are combined with an insecticide, pesticide, and/or fungicide compound or composition and result in a decreased dust profile during planting.

In an aspect, a composition described herein includes one or more of the following and combinations thereof:
(a) oil;
(b) wetting agent; and
(c) dispersing agent.

In yet another aspect, a composition described herein includes one or more of the following and combinations thereof:
(a) oil;
(b) wetting agent; and
(c) binder.

In an aspect, a composition described herein includes one or more of the following and combinations thereof:
(a) film forming compound;
(b) binder;
(c) oil;
(d) wetting agent; and
(e) dispersing agent.

In another aspect, the disclosure provides for a composition comprising one or more of the following and combinations thereof:
(a) poly(vinyl alcohol)/poly(vinyl pyrrolidone) ("PVP-PVA") copolymer;
(b) polyurethane composition or dispersion;
(c) ethoxylated fatty acid;
(d) sorbitan monooleate;
(e) alkyl alcohol with an ethylene oxide/propylene oxide;
(f) ethoxylated oleyl alcohol; and
(g) oil.

In another aspect, the disclosure provides for a composition comprising one or more of the following and combinations thereof:
(a-1) poly(vinyl alcohol)/poly(vinyl pyrrolidone) ("PVP-PVA") copolymer;
(b-2) polyurethane composition or dispersion;
(c-3) ethoxylated fatty acid;
(d-4) sorbitan monooleate;
(e-5) alkyl alcohol with an ethylene oxide/propylene oxide;
(f-6) ethoxylated oleyl alcohol;
(g-7) mineral oil; and
(h-8) vegetable oil.

In another aspect, the disclosure provides for a dust reducing composition comprising components "a-1" to "h-8" set forth in Table 2 and Table 3. As set forth in Tables 2 and 3, the amount of each respective component (in samples 1-11) is represented in "weight percent." Each sample exhibits a reduced dust profile relative to a seed sample that is not treated with the components set forth in Tables 1 and 2.

TABLE 1

| Sample | a-1 | b-2 | c-3 | d-4 | e-5 | f-6 | g-7 | h-8 |
|--------|-----|------|------|------|------|------|------|-------|
| 1 | 1-8 | 6-15 | 0 | 2-10 | 2-10 | 2-10 | 0 | 0 |
| 2 | 1-8 | 0 | 2-10 | 2-10 | 2-10 | 0 | 0 | 0 |
| 3 | 0 | 6-15 | 2-10 | 2-10 | 0 | 0 | 0 | 12-25 |
| 4 | 1-8 | 6-15 | 2-10 | 0 | 0 | 0 | 6-15 | 0 |
| 5 | 1-8 | 6-15 | 0 | 0 | 0 | 2-10 | 0 | 12-25 |
| 6 | 1-8 | 0 | 0 | 0 | 2-10 | 0 | 6-15 | 12-25 |
| 7 | 0 | 0 | 0 | 2-10 | 0 | 2-10 | 6-15 | 0 |
| 8 | 0 | 0 | 2-10 | 0 | 2-10 | 2-10 | 0 | 12-25 |
| 9 | 0 | 6-15 | 0 | 2-10 | 2-10 | 0 | 6-15 | 12-25 |
| 10 | 1-8 | 0 | 2-10 | 2-10 | 0 | 2-10 | 6-15 | 12-25 |
| 11 | 0 | 6-15 | 2-10 | 0 | 2-10 | 2-10 | 6-15 | 0 |

TABLE 2

| Sample | a-1 | b-2 | c-3 | d-4 | e-5 | f-6 | g-7 | h-8 |
|--------|------|------|------|------|------|------|-----|-----|
| 1 | 1-10 | 5-25 | 0 | 2-15 | 2-15 | 2-15 | 0 | 0 |
| 2 | 1-10 | 0 | 2-15 | 2-15 | 2-15 | 0 | 0 | 0 |

TABLE 2-continued

| Sample | a-1 | b-2 | c-3 | d-4 | e-5 | f-6 | g-7 | h-8 |
|---|---|---|---|---|---|---|---|---|
| 3 | 0 | 5-25 | 2-15 | 2-15 | 0 | 0 | 0 | 5-40 |
| 4 | 1-10 | 5-25 | 2-15 | 0 | 0 | 0 | 1-20 | 0 |
| 5 | 1-10 | 5-25 | 0 | 0 | 0 | 2-15 | 0 | 5-40 |
| 6 | 1-10 | 0 | 0 | 0 | 2-15 | 0 | 1-20 | 5-40 |
| 7 | 0 | 0 | 0 | 2-15 | 0 | 2-15 | 1-20 | 0 |
| 8 | 0 | 0 | 2-15 | 0 | 2-15 | 2-15 | 0 | 5-40 |
| 9 | 0 | 5-25 | 0 | 2-15 | 2-15 | 0 | 1-20 | 5-40 |
| 10 | 1-10 | 0 | 2-15 | 2-15 | 0 | 2-15 | 1-20 | 5-40 |
| 11 | 0 | 5-25 | 2-15 | 0 | 2-15 | 2-15 | 1-20 | 0 |

In another aspect, one or more of the following compounds and compositions is used in a method described herein. In another aspect, one or more, two or more, three or more, four or more, five or more, six or more, seven or more, or eight or more of the below compounds or compositions are used in a method or composition described herein.

TABLE 3

| Chemical Structure | Component Example |
|---|---|
| Fatty (18) alcohol ethoxylate | Genapol O100 |
| PO-EO butanol | Antarox B848 |
| Fatty acid ethoxylate | Ninex MT615 |
| PVP-PVA copolymer, 50% solution | Luvitec VA64 W |
| Polyurethane dispersion | Impranil DLN W50 |
| Pressure sensitive acrylic polymer | Acronal A240 |
| Polyether modified polysiloxan, slipping agent | Tegopren 3158 |
| Modified polyoxyethylene terephthalate (POET) | SRP170 |
| Similar to tegopren | Break thru OE441 |
| Triglyceride monooleate | Glycolube 740KFG 64D |
| Mixture of 6 ingredients (Linseed 16, Tufflo 8, Genapol 6, Ninex 6, Antarox 6, Luvitec 4) | |
| PVP 9000 Mw | Luvitec K90 |

In an aspect, one or more of a polyether-modified polysiloxane, polyvinylpyrrolidone, or triglyceride Monooleate are utilized in a composition or methods described herein. In another aspect, one or more of Break-Thru OE441, Tegopren 3158, Luvitec K90 (10%), Glycolube 740 KFG, and/or Break Thru OE 440 are utilized in a composition or methods described herein. In another aspect, a method described herein comprises, consists of, or consists essentially of Break-Thru OE441, Tegopren 3158, Luvitec K90 (10%), Glycolube 740 KFG, and/or Break Thru OE 440.

In another aspect, one or more, two or more, three or more, four or more, five or more, six or more, seven or more, or eight or more compounds or components are used in a method or composition described herein.

In an aspect, a film forming compound is a compound that forms a solid layer on a seed surface. In another aspect, a film forming compound is a compound that forms a solid layer when slurry dries on a seed surface. Without being limited, a film forming compound is selected from the group consisting of polyurethane compound or composition, a polyurethane dispersion, an anionic aliphatic polyester-polyurethane dispersion, a water-soluble polymer, a polyvinylpyrrolidone (PVP polymer), Impranil® DLN 50 (Bayer), Impranil® DLN W 50 (Bayer), Luvitec® VA 64 (BASF), and Luvitec® line of products.

In an aspect, a binder is a compound or composition that binds particles on seed surface. In another aspect, a binder is a compound or composition that physically or chemically binds solid particles on seed surface. Without being limited, a binder can be selected from adhesion agents such as acrylic polymer (ACRONAL Series, BASF), vinyl acetate polymers, or styrene and butadiene copolymers latex compound (STYROFAN and STYRONAL Series, BASF).

In an aspect, an oil is selected from the group consisting of, for example, mineral oil, mineral processing oil, vegetable oil, natural oil, synthetic oil, refined vegetable oil, plant oil, linseed oil, and Tufflo® 100 (Calumet).

In an aspect, a "wetting agent" refers to compounds added to a liquid in small quantities in order to enhance the spreading of the liquid on a surface or the penetration of the liquid into the solid particles in the liquid or/and the solid substrate that gets in contact with the liquid. Thus an effective wetting agent for coating can be a surfactant that has affinity groups to solid particles and able to replace air and moisture that traps in the solid particles in order to spread and penetrate to the surface of the solid particles. In an aspect, wetting agents are surface active compounds having low molecular weight, less than 4000 g/mol.

Wetting agents can be anionic, cationic or nonionic surface active compounds. Nonionic compounds can be selected from modified polysiloxane esters, sorbitan esters, polyoxyethylene sorbitan esters, aliphatic alcohol alkoxylates, oxo alcohol alkoxylates, aromatic alcohol alkoxylates, oil alkoxylates, fatty alcohol alkoxylates and fatty acid alkoxylates. Without being limited, examples of modified polysiloxane esters are Tegropren and BreakThru series (EVONIK). Examples of sorbitan esters and polyethoxylated sorbitan esters are Span and Tween series (CRODA). Polyalkoxylated, preferably polyethoxylated, saturated and unsaturated aliphatic alcohols are commercially available, for example as GENAPOL X, GENAPOL OA, GENAPOL OX, GENAPOL UD, GENAPOL LA and GENAPOL O series (CLARIANT), CROVOL M series (CRODA) or as LUTENSOL series (BASF), or are obtainable therefrom by etherification, for example GENAPOL X060 and GENAPOL X100. Polyalkoxylated, preferably polyethoxylated, arylalkylphenols could be SOPROPHOR BSU (RHODIA), EMULSOGEN TS series (CLARIANT) or HOE S 3474 (CLARIANT). Polyalkoxylated, preferably polyethoxylated, alkylphenols have available commercial products are SAPOGENAT T series (CLARIANT). Examples of polyalkoxylated, preferably polyethoxylated, hydroxyfatty acids or glycerides are Ninex MT-615 (STEPAN), EMULSOGEN EL series (CLARIANT) or the AGNIQUE CSO series (BASF).

In an aspect, a dispersing agent is a material capable of keeping suspended particles from coagulating or aggregating. In another aspect, a dispersing agent creates a barrier between active ingredients. In an aspect, the molecular weight of dispersing agent can vary from 500 to 250000 g/mol. In an aspect, dispersing agents can also be anionic, cationic or nonionic surface active compounds. For example, nonionic compounds can be selected from ethylene oxide and propylene oxide block co-polymers, for example the ANTAROX B/848 (CRODA), GENAPOL PF series (CLARIANT), the PLURONIC series (BASF), the SYNPERONIC PE series (CRODA), or the TOXIMUL series (STEPAN). Nonionic dispersing agents can also be selected from polyethoxylated alcohols, polyethoxylated triglycerides and alkyl polysaccharides, (AGNIQUE PG Series from BASF). Dispersing agents with high molecular weight are commonly called polymeric surface active ingredients. The most commonly used polymeric dispersants are ethoxylated polymethacrylate graft copolymer (ATLOX 4913, CRODA) and alkylated vinylpyrrolidone copolymers and polyvinylpyrrolidone (LUVITEC Series from BASF, AGRIMER series from ASHLAND) and vinylacetate/vinylpyrrolidone copolymers (LUVITEC VA64, BASF). Polyvinyl alcohols can also be used as dispersing agents.

In an aspect, a dust reducing, washing, and/or additive composition comprises at least about 0.01%, at least about 0.025%, at least about 0.05%, at least about 0.1%, at least about 0.25%, at least about 0.5%, at least about 1%, at least about 2%, at least about 2.5%, at least about 5%, at least about 6%, at least about 7%, at least about 8%, at least about 9%, at least about 10%, at least about 12.5%, at least about 15%, at least about 20%, at least about 25%, at least about 30%, at least about 35%, at least about 40%, or at least about 50%, at least about 75% or more by weight of a compound or component described herein. In an aspect, a component is an oil, wetting agent, dispersing agent, film forming compound, binder, or component described in the Tables, Figures, or Examples described herein.

In another aspect, a dust reducing, washing, and/or additive composition comprises about 0.01%, about 0.025%, about 0.05%, about 0.1%, about 0.25%, about 0.5%, about 1%, about 2%, about 2.5%, about 5%, about 6%, about 7%, about 8%, about 9%, about 10%, about 12.5%, about 15%, about 20%, about 25%, about 30%, about 35%, about 40%, about 50%, or about 75% or more by weight of a compound or component described herein. In an aspect, a component is an oil, wetting agent, dispersing agent, film forming compound, binder, or component described in the Tables, Figures, or Examples described herein.

In another aspect, a dust reducing, washing, and/or additive composition comprises about 0.001% to about 0.1%, about 0.0025% to about 0.25%, about 0.1% to about 1%, about 0.1% to about 2.5%, about 0.5% to about 2.5%, about 1% to about 2%, about 1% to about 3%, about 1% to about 5%, about 1% to about 10%, about 2% to about 10%, about 5% to about 10%, about 5% to about 20%, about 10% to about 15%, about 15% to about 20%, about 10% to about 25%, about 10% to about 50%, about 25% to about 50%, or about 20% to about 80%, and about 95% or more by weight of a compound or component described herein. In an aspect, a component is an oil, wetting agent, dispersing agent, film forming compound, In an aspect, a composition described herein is one set forth in Tables 1 and 2.

In another aspect, a composition described herein can further include a surfactant, colorant, wax, epoxy, UV curable coating, seed over-coat composition, and/or filler.

In another aspect, an active agent can be added to or incorporated into a composition described herein. In an aspect, an active agent is a compound or composition exhibiting insecticidal, pesticidal, or fungicidal properties. In another aspect, an active agent is a compound or composition with neonicotinoid properties. In an aspect, an active agent is selected from the group consisting of acetamiprid, clothianidin, dinotefuran, imidacloprid, nitenpyram, thiacloprid, thiamethoxam, Nipsit INSIDE® (Valent), Platinum® (Syngenta), Admire® Pro (Bayer CropScience), Cruiser (Syngenta), Gaucho (Bayer CropScience), Leverage® (Bayer CropScience), Actara (Syngenta), Venom (Valent), Provado® (Bayer CropScience), Alias (Mana), Pasada (Mana), Couraze (Cheminova), Assail® (DuPont), Poncho®/VOTiVO™ (Bayer CropScience), Poncho® 1250+VOTiVO™ (Pioneer), and/or Requiem® (Agroquest). In an aspect, the active agent is applied to a seed and the seed is subsequently coated with a lubricant compound.

In an aspect, insecticidal dust, pesticidal dust, or fungicidal dust is dust from one or more of the following actives: acetamiprid, clothianidin, dinotefuran, imidacloprid, nitenpyram, thiacloprid, thiamethoxam, Nipsit INSIDE® (Valent), Platinum® (Syngenta), Admire® Pro (Bayer CropScience), Cruiser (Syngenta), Gaucho (Bayer CropScience), Leverage® (Bayer CropScience), Actara (Syngenta), Venom (Valent), Provado® (Bayer CropScience), Alias (Mana), Pasada (Mana), Couraze (Cheminova), Assail® (DuPont), Poncho®/VOTiVO™ (Bayer CropScience), Poncho® 1250+VOTiVO™ (Pioneer), and/or Requiem® (Agroquest). In an aspect, the active agent is applied to a seed and the seed is subsequently coated with a composition described herein. In another aspect, "dust" can include any active agent coated on a seed that is emits a particulate or "dust." In another aspect, dust is released during the planting process.

In an aspect, a composition described herein includes a mixture or combination of composition described herein and treatment agent described herein.

In another aspect, a composition or method described herein does not include an inorganic lubricant composition. Inorganic compounds, for example talc and graphite, encompass compounds such as carbides, carbonates, simple oxides of carbon, cyanides, and allotropes of carbon.

In an aspect, a composition or method described herein does not include talc. In another aspect, a composition or method described herein does not include graphite or graphite blends. In yet another aspect, a composition or method described herein does not include blends of graphite and/or talc. In another aspect, a composition or method described herein contains trace amount of talc or graphite. In another aspect, a composition or method described herein contains less than about 5%, less than about 10%, less than about 20%, less than about 20%, less than about 30%, less than about 40%, or less than about 50% by weight of talc, graphite, or a combination of talc or graphite.

In yet another aspect, a composition described herein may be blended with inert materials to improve handling or packaging, for example, silica, starches (natural and derived), clays, and other minerals.

In an aspect, a composition described herein is applied as a powder or liquid to a seed. In an aspect, a composition described herein is capable of providing lubricity and/or improved dust reduction at a lower use rate as compared to conventional lubricants, such as talc or graphite.

In another aspect, a composition described herein provides an increased level of dust reduction relative to traditional lubricant compositions, such as talc or graphite. In an aspect, a composition described herein is also effective at lower application rates than talc or graphite.

In an aspect, a composition described herein is formulated as a particle, micro-particle, or nano-particle. In another aspect, a particle described herein is from about 0.01 µm to about 1 µm, from about 0.1 µm to about 2 µm, from about 0.5 µm to about 3 µm, from about 2 µm to about 4 µm, from about 1 µm to about 10 µm, from about 2 µm to about 5 µm, from about 3 µm to about 8 µm, from about 2 µm to about 10 µm, from about 10 µm to about 25 µm, from about 10 µm to about 100 µm, or from about 10 µm to about 500 µm.

In another aspect, a composition described herein is formulated in the following manner:

| Mechanism | Approach | Methods |
|---|---|---|
| Immobilization of Active Ingredients on Seed Surface | Built-In Formulation | Oil, for example, a Mineral Oil Oil, for example, a Refined Vegetable Oil Adhesion Ingredient, for |

-continued

| Mechanism | Approach | Methods |
|---|---|---|
| | Film Coating | example, a Binder Surfactant/solvent combination Polymer, Wax, and/or Colorant Reactive Seed Coating (Epoxy, UV curable coating) |
| | Pelletize | Over-Coat seeds with layer(s) of polymer, filler, or other additive |
| | Particle size reduction | Submicron particles |
| Isolate/Protect Each Active Ingredient Particles | A. I. particle isolation | Encapsulation |
| Deliver Active Ingredient into Seeds | Nanotech | nanoformulation |

In an aspect, the methods and compositions described herein reduce dust by about 5% to about 20%, about 20% to about 60%, about 40% to about 70%, about 50% to about 90%, about 60% to about 80%, about 65% to about 95%, about 80% to about 95%, or about 5%, about 15%, about 25%, about 40%, about 50%, about 60%, about 70%, about 80%, about 90%, or about 95%, or about 5% or more, about 15% or more, about 25% or more, about 40% or more, about 50% or more, about 60% or more, about 70% or more, about 80% or more, about 90% or more, or about 95% or more. In yet another aspect, the dust emissions, insecticidal dust emissions, pesticidal dust emissions, or fungicidal dust emissions is reduced relative to traditional dust reduction compounds or compositions.

In an aspect, a composition described herein is applied to a seed in an amount that is effective to reach the desired property.

In an aspect, a composition described herein is applied to a seed at a rate of about 0.1-5.0 oz/cwt (ounces/hundredweight), about 0.5-4.0 oz/cwt, about 1.0-3.5 oz/cwt, about 1.5-3.0 oz/cwt, about 2.0-3.0 oz/cwt, about 2.0-2.5 oz/cwt, or about 0.2 oz/cwt, about 0.5 oz/cwt, about 0.75 oz/cwt, about 1.0 oz/cwt, about 1.5 oz/cwt, about 2.0 oz/cwt, about 2.5 oz/cwt, about 3.0 oz/cwt, about 3.5 oz/cwt, about 4.0 oz/cwt, about 4.5 oz/cwt, about 5.0 oz/cwt, or about 0.2 oz/cwt or more, about 0.5 oz/cwt or more, about 0.75 oz/cwt or more, about 1.0 oz/cwt or more, about 1.5 oz/cwt or more, about 2.0 oz/cwt or more, about 2.5 oz/cwt or more, about 3.0 oz/cwt or more, about 3.5 oz/cwt or more, about 4.0 oz/cwt or more, about 4.5 oz/cwt or more, or about 5.0 oz/cwt, about 6.0 oz/cwt or more, about 7.0 oz/cwt or more, or about 8.0 oz/cwt, about 9.0 oz/cwt, about 1.0 oz/cwt or more, or about 15 oz/cwt, about 20.0 oz/cwt or more. In yet another aspect, a composition described herein is applied to a seed in a manner sufficient to convey the desired property.

In an aspect, a composition described herein is applied to a seed in a single application step. In another aspect, a composition described herein is applied in multiple application steps. In yet another aspect, a composition described herein is applied in one, two, three or more application steps to a seed. In another aspect, a method described herein excludes multiple application steps. In an aspect, the methods described herein include a first sequential application of a treating agent described herein to a seed followed by a second application of lubricant composition described herein to a seed.

Seeds which can be treated by the methods described herein include, for example, seeds that are treated with insecticides, pesticides, or fungicides that are harmful to pests or insects, for example, bees. Seeds may include any agricultural or vegetable seeds that are planted through a vacuum planter, including wherein talc may be used as a planter lubricant. In an aspect, the seed is selected from the group consisting of a corn seed, cotton seed, sorghum seed, oat seed, rye seed, rice seed, rapeseed, canola seed, barley seed, soybean seed, or vegetable seed. In an aspect, the seed is corn seed. Examples of wheat seeds include, for example, Found Boundary, Bullet, or Oaks wheat varieties. Examples of corn seeds capable of being used in the methods described herein include, for instance, sweet corn (for example, *zea mays* convar. *saccharata* var. *Rugosa*), silver queen corn, golden bantam, early sunglow, indian corn, sugar corn, pole corn, field corn, dent corn, flint corn, flour corn, blue corn (for example, *Zea mays amylacea*), pop corn, and waxy corn.

Among the plants that can be protected by the method according to the invention, mention may be made of major field crops like corn, soybean, cotton, *Brassica* oilseeds such as *Brassica napus* (e.g. canola), *Brassica rapa*, *B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

Seeds may be treated with the described compositions by applying the compositions directly to the seed. In another embodiment, the seed may be treated indirectly, for example by treating the environment or habitat in which the seed is exposed to Conventional treatment methods may be used to treat the environment or habitat including dipping, spraying, fumigating, chemigating, fogging, scattering, brushing on, shanking or injecting.

In an aspect, a compound or composition described herein is applied, incorporated, or coated on a seed, plant part, or plant thereof.

In another aspect, the disclosure provides for a kit comprising, consisting essentially of, or consisting of any of the compositions disclosed herein. In an aspect, the kit includes any of the combination of compositions described in Examples 1-9 or Tables 1-6. In another aspect, the kit provides for the compositions described in Examples 1-9 or Tables 1-6, applied in a manner that is consistent with the methodology of these examples and figures. In another aspect, the kit provides instructions or guidance regarding the use of the compositions or methods described herein.

In an aspect, the kit includes instructions describing the methodology described herein. In another aspect, the kit includes instructions describing the methodology set forth in any of Examples 1-9 or Tables 1-6. In an aspect, the instructions are included with the kit, separate from the kit, in the kit, or are included on the kit packaging. In yet another aspect, the instructions provide for application of a dust reducing composition at before, after, or at the same time as planting.

In an aspect, a dust reducing, additive, or washing compound or composition described herein is in the same bag or package or a separate bag or package from an insecticide, fungicide, and/or pesticide compound or composition.

The following examples serve to illustrate certain aspects of the disclosure and are not intended to limit the disclosure.

EXAMPLES

Example 1

Example 1 sets forth the results from experiments comparing the influence of different compositions on dust level.

The compounds and compositions evaluated are listed in Table 4. They represent a range of different components, for example:

1) Film formers which form a solid layer when slurry dries on seed surface, polyurethane dispersion, PVP polymers;
2) Binders—physically or chemically bind solid particles on seed surface, styrene-butadyne polymeric latex;
3) Oils—mineral oils, plant oils (for example, linseed oil);
4) Wetting agents—materials (surfactants) making hydrophobic seed surface more hydrophilic, fatty alcohol ethoxylate, and polysiloxane; and
5) Dispersing agents—materials keeping suspended particles from coagulation or aggregation, alkyl alcohol with (EO-PO)n chain.

TABLE 4

| Ingredient | Example of Chemistry and Functions |
|---|---|
| Luvitec ® VA 64 | PVP-PVA copolymer, film forming agent, binder, less water absorbent than PVP |
| Impranil ® DLN 50 | Polyurethane dispersion, film forming agent, binder |
| Ninex ® MT-615 | Ethoxylated fatty acid, 15 EO, emulsifier |
| Tween ® 80 | Sorbitan monooleate, C24, 20EO, emulsifier |
| Antarox ® B/848 | Butyl capped EO-PO copolymer, dispersing agent; multipurpose emulsifier |

TABLE 4-continued

| Ingredient | Example of Chemistry and Functions |
|---|---|
| Genapol ® O-100 | Nonionic surfactant; C 16-18 Fatty alcohol polyglycol ether with 10 mol EO |
| Tufflo ® 100 | Mineral processing oil |
| Linseed oil | Vegetable oil, used with paint |

Example 2

Example 2 sets forth the results of testing various adjuvant formulations on wheat seeds together with Imidacloprid 600 grams/liter model.

In order to evaluate the properties of the compositions, individual components were mixed with Imidacloprid 600 g/L before treating seeds. Each component was weighted and mixed with water to make a 100 parts of adjuvant emulsion in water.

Fifty (50) parts of prepared emulsion was mixed with 50 parts of Imidacloprid to make a 100 parts formulation. Then, 7.1 parts of above formulation, 0.7 parts of red colorant and 9.9 parts of water were weighted to prepare 17.7 parts of slurry. For 515 grams of wheat seeds, a 4 mL (cc) of prepared slurry was used. For 515 grams of corn seeds, a 4.35 mL (cc) prepared slurry was used.

Example 3

Example 3 sets forth the results of testing the adjuvant formulations on corn seed.

Example 4

Example 4 sets forth the results of testing the adjuvant formulations on physical stability of the slurry formulation.

The physical stability of the formulations prior to seed application was assessed with a rating of 1 for best appearance and 10 for worst appearance. The data is exhibited in Table 5.

TABLE 5

| Components | Rating |
|---|---|
| 1 | 5 |
| 2 | 4 |
| 3 | 8 |
| 4 | 8 |
| 5 | 6 |
| 6 | 7 |
| 7 | 7 |
| 8 | 6 |
| 9 | 8 |
| 10 | 1 |
| 11 | 7 |
| 12 | 8 |

The higher absolute number indicates greater impact of that component on physical stability.

Example 5

Example 5 sets forth single component testing using a Imidacloprid 600 grams/liter model formulation testing.

Samples for the Imidacloprid 600 g/L system were prepared as follows: For 100 lb wheat seeds, a 12 oz slurry containing G600 (2.4 oz); Red colorant (0.5 oz); Additive (X oz); Water (9.1-X) oz. For 515 g wheat seeds, 4 mL (cc) prepared slurry was used.

The dust levels are described in terms of grams per 100 kg Bullet wheat seed treated with imidicloprid at a concentration of 600 grams per liter.

Example 6

Example 6 sets forth experimental results using Imidacloprid 350 grams/liter as a model formulation system.

Sample preparation for the Imidacloprid 350 g/L system was as follows: For dust level evaluation, components were mixed with Imidacloprid 600 g/L before treating seeds (PSM series). Each component or mixture of components was weighted before mixing with water and Imidacloprid 600 g/L. Then, 10, 14, 19 or 28 parts of ingredient or mixture of ingredient was mixed with 61.4 parts of Imidacloprid 600 g/L and corresponding amount of water to make a 100 parts of Imidacloprid 350 g/L formulation. Next, 9.9 parts of the above formulation, 1.2 parts of red colorant and 15.5 parts of water were assembled to prepare 26.6 parts of slurry. For 515 grams corn or wheat seeds, 4.35 mL prepared slurry was used.

Results are shown in terms of grams dust per 100 kg Oakes wheat seed to compare the effect of a variety of additives.

Results are shown in terms of grams dust per 100 kg Bullet wheat seed to compare the influence of a variety of additives.

Results are shown in terms of grams dust per 100 kg corn seed to compare the influence of a variety of additives.

Example 7

Example 7 sets forth experimental results using Imidacloprid plus Thiodicarb 150+450 g/L as a formulation model system.

Sample preparation was as follows: For design of experiment screening and combined influence evaluation, each candidate was weighted and mixed with active ingredients, water, surfactants and other formulants to make a water-based mixture; the mixture was milled with Eiger mill (bead mill); Rheology modifier (Kelzan) and water were added in the resulted millbase to make the final 600 g/L formulation. Then, 3.5 volume parts of 600 g/L formulation, 0.1 volume parts of blue colorant and 1.4 volume parts of water were mixed to make a slurry ready to treat seeds. For 500 g corn seeds, 5.0 mL (~5.75 g) prepared slurry was used.

In Table 6, the components tested are shown.

TABLE 6

| A | Alcohol Type | Propylene Glycol | Glycerin |
|---|---|---|---|
| B | Alcohol Level | 8 | 4 |
| C | Morwet D425 | 0.5 | 0 |
| D | Film former 1 | Luvitec VA64 | Genapol O-100 |
| E | Film former Level | 4 | 0 |
| F | Film former 2 | Styronal 778 | Impranil DLN 50 |
| G | Film former 2 Level | 4 | 0 |
| H | Kelzan S (2%) | 0.1 | 0.05 |

For the column labeled "8/4", a positive sign indicates 8% and a negative sign indicates 4% and denotes the weight % amount of wither propylene glycol or glycerin. For the column labeled D425 (0.5/0), a positive sign indicates presence of Morwet D425 in an amount of 0.5% wt and a negative sign indicates the absence of Morwet D425. For the column labeled VA64 (SLN 50)/O100, a positive sign indicates the presence of Luvitec VA64 and a negative sign indicates the presence of Genapol O-100. For the next column, a positive sign indicates 4% wt and a negative sign indicates 0% wt of either Luvitec 64 or Genapol O-100. In the column labeled S778/IMN (DPN 50), a positive sign indicates the presence of Styronal 778 while a negative sign indicates the presence of Impranil DLN 50. For the next column, a positive sign indicates 4% wt and a negative sign indicates 0% wt of either Styronal 778 or Styronal 778. For the column labeled KEL (0.1/0.5), a positive sign indicates the presence of Kelzan S (2%) at 0.1% while a negative sign indicates the presence of Kelzan S (2%) at 0.05%.

The higher absolute number indicates greater impact of that ingredient on dust control.

Example 8

Example 8 sets forth the impact of particle size of the active ingredient on dust levels.

As can be seen, there is a direct correlation between particle size and dust levels. As active ingredient particle size increases, the amount of dust on the seed increases.

Example 9

Example 9 sets forth an analysis of surface coverage of the tested formulations and dust level.

Wheat or corn seeds are treated with the seed treatment composition (slurry) by a Hege seed treatment device, where the slurry is atomized and coat the seeds uniformly.

The treated seeds are kept open to ambient environment for 5 days and then stored in a constant climate chamber for minimum of 48 hours at 20° C.±2° C. and 50%±10% relative humidity. The amount of dust coming off the seeds is measured using a Heubach dustmeter. About 100 grams of treated seeds are placed in a chamber. The chamber is rotated to generate friction among the seeds and between the chamber wall and the seeds, which simulate the handling of the treated seeds. A constant airflow passes through the chamber controlled by a precision vacuum system. The flow of air carries air borne particles through a coarse filter separator onto a glass fiber filter disc. The Heubach dust values can be calculated by measuring the weight of filter disc before and after the evaluation test.

A qualitative assessment of seed coating using microscopic imaging was conducted.

Treated seeds with lower level of dust have a higher percentage of surface coverage of formulation with both ridges and valleys covered.

The invention claimed is:

1. A method of reducing or controlling seed dust comprising treating a seed with a dust reducing composition comprising
    (a) one or more active agents selected from the group consisting of an insecticide, pesticide, and fungicide;
    (b) a poly(vinyl alcohol)/poly(vinyl pyrrolidone) copolymer or poly(vinyl acetate)/poly(vinyl pyrrolidone) copolymer;
    (c) an ethoxylated fatty acid;
    (d) a sorbitan monooleate;
    (e) an ethoxylated and propoxylated alkyl alcohol;
    (f) an ethoxylated oleyl alcohol; and
    (g) an oil; and
    (h) a polyurethane composition or dispersion and
reducing or controlling dust on the seed.

2. The method of claim 1, wherein said one or more active agents is selected from the group consisting of acetamiprid, clothianidin, dinotefuran, imidacloprid, nitenpyram, thiacloprid, thiamethoxam, and combinations thereof.

3. The method of claim 1, wherein said seed is selected from the group consisting of a corn seed, cotton seed, sorghum seed, oat seed, rye seed, rice seed, rapeseed, canola seed, barley seed, soybean seed, and vegetable seed.

4. The method of claim 1, wherein said seed is treated with said dust reducing composition prior to planting.

5. The method of claim 1, wherein seed dust is reduced or controlled during seed processing, seed coating, seed transportation, seed storage, seed planting, or combinations thereof.

6. The method of claim 1, wherein said seed is coated with said dust reducing composition.

7. The method of claim 1, wherein said method reduces seed dust by about 20% to about 60%.

8. The method of claim 1, wherein said composition is applied to the seed at a rate of about 0.1 to 5.0 ounces/hundredweight.

9. The method according to claim 1, wherein the ethoxylated and propoxylated alkyl alcohol is a butyl capped copolymer of ethylene oxide (EO) and propylene oxide (PO).

10. The method of claim 1, wherein the dust reducing composition further comprises an acrylic polymer.

11. The method of claim 1, wherein the one or more active agents comprises imidacloprid.

12. The method of claim 1, wherein the one or more active agents comprises thiacloprid.

* * * * *